United States Patent
Ohnishi et al.

(10) Patent No.: US 7,227,036 B2
(45) Date of Patent: Jun. 5, 2007

(54) PRODUCTION PROCESS OF AMINOMETHYL GROUP-CONTAINING BENZAMIDE COMPOUND

(75) Inventors: Yutaka Ohnishi, Kawasaki (JP); Hideo Miyata, Kawasaki (JP); Kimitaka Ohshiro, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/515,215

(22) PCT Filed: May 2, 2003

(86) PCT No.: PCT/JP03/05634

§ 371 (c)(1),
(2), (4) Date: Nov. 22, 2004

(87) PCT Pub. No.: WO03/097579

PCT Pub. Date: Nov. 27, 2003

(65) Prior Publication Data

US 2005/0203313 A1    Sep. 15, 2005

Related U.S. Application Data

(60) Provisional application No. 60/383,111, filed on May 28, 2002.

(30) Foreign Application Priority Data

May 22, 2002  (JP) .............................. 2002-147042

(51) Int. Cl.
  *C07C 231/06*  (2006.01)
(52) U.S. Cl. ....................... 564/124; 564/126; 564/129
(58) Field of Classification Search ................ 564/124, 564/126, 129
  See application file for complete search history.

(56) References Cited

U.S. PATENT DOCUMENTS

| 4,022,830 A | | 5/1977 | Watts, Jr. | |
| 6,100,427 A | * | 8/2000 | Bezuidenhout et al. | ..... 564/127 |
| 6,521,794 B2 | * | 2/2003 | Hirota | ..... 564/442 |

FOREIGN PATENT DOCUMENTS

| EP | 0989115 A2 | | 3/2000 |
| JP | 2001-79406 | * | 3/2001 |
| WO | 98/33767 | * | 8/1998 |
| WO | WO 02085860 A1 | | 10/2002 |

OTHER PUBLICATIONS

Database Crossfire Beilstein 'online', Beilstein Institut Zur Forderung der Chemischen Wissenschaften, Frankfurt am Main, DE, Database accession No. Reaction ID 40767, XP002251925 (2001).
Database Crossfire Beilstein 'online', Beilstein Institut Zur Forderung der Chemischen Wissenschaften, Frankfurt am Main, DE, Database accession No. Reaction ID 352148, XP002251926 (2001).
Synthesis, vol. 12, pp. 949-950 (1989).
J. American Chem. Soc., vol. 39, pp. 103-109 (1917).

* cited by examiner

*Primary Examiner*—Shailendra Kumar
(74) *Attorney, Agent, or Firm*—Sughrue Mion, PLLC

(57) ABSTRACT

There is provided a process for producing an aminomethyl group-containing benzamide compound represented by the general formula (II): wherein —CONH2 and —X represent a substituent on the benzene ring and —CONH2 exists at the meta- or para-position of —CH2NH2, and X and n are as defined below, which comprises hydrating an aminomethyl group-containing benzonitrile compound represented by the general formula (I): wherein —CN and —X represent a substituent on the benzene ring and —CN exists at the meta- or para-position of —CH2NH2, X represents a chlorine atom or a fluorine atom, and n represents an integer of 0 to 4, provided that, when n is 2 or more, X may be the same or different

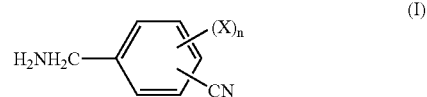

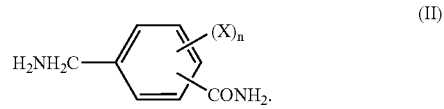

3 Claims, No Drawings

PRODUCTION PROCESS OF AMINOMETHYL GROUP-CONTAINING BENZAMIDE COMPOUND

CROSS-REFERENCE TO RELATED APPLICATIONS

This application is a 371 of PCT/JP03/05634, filed May 2, 2003; which claims benefit of 60/383,111, filed May 28, 2002.

FIELD OF THE INVENTION

The present invention relates to a production process of an aminomethyl group-containing benzamide compound. The aminomethyl group-containing benzamide compound is useful as intermediates for medicaments, pesticides, liquid crystals and functional polymeric monomer.

BACKGROUND OF THE INVENTION

As the production process of an aminomethyl group-containing benzamide compound, several processes are known. Examples of the production process of 4-aminomethylbenzamide include a process of suspending 4-cyanobenzamide in ammonia-containing methanol and reacting the suspension at room temperature using $Rh/Al_2O_3$ as a catalyst (Unexamined Japanese Patent Publication (Kokai) No. 60-139670), a process for contact hydrogenation of 4-cyanobenzamide in the presence of ammonia using a sponge nickel catalyst (Unexamined Japanese Patent Publication (Kohyo) No. 8-505862) and a process of treating a hydrochloride of 4-aminomethylbenzoate ester with ammonia (U.S. Pat. No. 3,817,981).

The process using 4-cyanobenzamide as a starting material exhibits poor productivity because the reaction is conducted at low concentration and low yield. Also the process using 4-aminomethylbenzoate ester as a starting material does not exhibit good productivity because it requires a multi-stage reaction and a complicated operation in order to obtain the starting material.

An object of the present invention is to produce an aminomethyl group-containing benzamide compound with high purity, which is useful as intermediates for medicaments and pesticides, represented by the general formula (II):

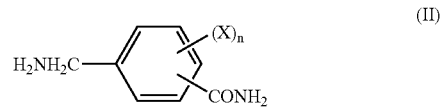

wherein —$CONH_2$ and —X represent a substituent on the benzene ring and exist at the meta- or para-position of —$CONH_2$—$CH_2NH_2$, X represents a chlorine atom or a fluorine atom, and n represents an integer of 0 to 4, provided that, when n is 2 or more, X may be the same or different, with high yield using an industrially useful process.

The present inventors have found that the above object can be achieved by converting a cyano group (—CN) on the benzene ring into an amide group (—$CONH_2$) using, as a starting material, an aminomethyl group-containing benzonitrile compound represented by the general formula (I):

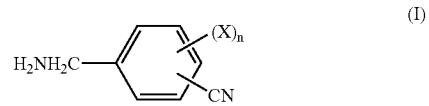

wherein —CN and —X represent a substituent on the benzene ring and —CN exists at the meta- or para-position of —$CH_2NH_2$, X represents a chlorine atom or a fluorine atom, and n represents an integer of 0 to 4, provided that, when n is 2 or more, X may be the same or different, and thus the present invention has been completed.

SUMMARY OF THE INVENTION

That is, the present invention is directed to the followings:

[1] A process for producing an aminomethyl group-containing benzamide compound represented by the general formula (II):

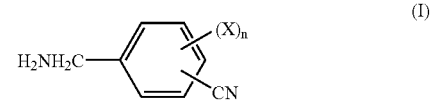

wherein —$CONH_2$ and —X represent a substituent on the benzene ring and —$CONH_2$ exists at the meta- or para-position of —$CH_2NH_2$, and X and n are as defined below, which comprises hydrating an aminomethyl group-containing benzonitrile compound represented by the general formula (I):

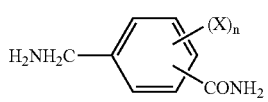

wherein —CN and —X represent a substituent on the benzene ring and —CN exists at the meta- or para-position of —$CH_2NH_2$, X represents a chlorine atom or a fluorine atom, and n represents an integer of 0 to 4, provided that, when n is 2 or more, X may be the same or different.

[2] The process according to [1], wherein the hydration is conducted in the presence of a concentrated sulfuric acid.

[3] The process according to [1], wherein the hydration is conducted in an alcohol solvent in the presence of a basic compound.

[4] The process according to [1], wherein the hydration is conducted in the presence of hydrogen peroxide.

[5] The process according to [1], wherein the hydration is conducted in the presence of a basic compound.

[6] The process according to [1], wherein the hydration is conducted using a sponge copper as a catalyst.

[7] The process according to [1], wherein the aminomethyl group-containing benzonitrile compound of the general formula (I) is m- or p-aminomethylbenzonitrile and the aminomethyl group-containing benzamide compound of the general formula (II) is m- or p-aminomethylbenzamide.

[8] The process for producing an aminomethyl group-containing benzamide compound according to any one of [1]

to [7], which uses an aminomethyl group-containing benzonitrile compound represented by the general formula (I):

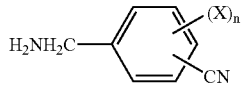

(I)

wherein —CN and —X represent a substituent on the benzene ring and —CN exists at the meta- or para-position of —CH$_2$NH$_2$, and X and n are as defined below, which is obtained by selectively reducing either of nitrile groups of a phthalonitrile compound represented by the general formula (III):

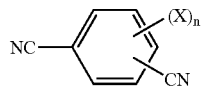

(III)

wherein —CN and —X represent a substituent on the benzene ring, two —CN (s) exist at the meta- or para-position, X represents a chlorine atom or a fluorine atom, and n represents an integer of 0 to 4, provided that, when n is 2 or more, X may be the same or different.

DETAILED DESCRIPTION OF THE INVENTION

The present invention will now be described in detail.

The aminomethyl group-containing benzonitrile compound represented by the general formula (I):

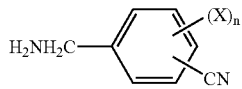

(I)

wherein —CN and —X represent a substituent on the benzene ring and —CN exists at the meta- or para-position of —CH$_2$NH$_2$, X represents a chlorine atom or a fluorine atom, and n represents an integer of 0 to 4, provided that, when n is 2 or more, X may be the same or different, used in the present invention can be produced easily in a large amount by the hydrogenation reaction of a one-side nitrile group of a corresponding dinitrile compound represented by the general formula (III):

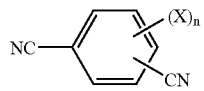

(III)

wherein —CN and —X represent a substituent on the benzene ring and two —CN(s) exist at the meta- or para-position, X represents a chlorine atom or a fluorine atom, and n represents an integer of 0 to 4, provided that, n is 2 or more, X may be the same or different. For example, p-aminomethylbenzonitrile and m-aminomethylbenzonitrile can be respectively obtained in a reaction yield of 80% by selectively hydrogenating a one-side nitrile moiety of terephthalonitrile and isophthalonitrile using a sponge nickel/cobalt catalyst pretreated with hydrogen (Japanese Unexamined Patent Publication (Kokai) No. 10-204048). 4-aminomethyl-2,3,5,6-tetrafluorobenzonitrile and 3-aminomethyl-2,4,5,6-tetrafluorobenzonitrile can be respectively produced by selectively hydrogenating a one-side nitrile moiety of tetrafluoroterephthalonitrile and tetrafluoroisophthalonitrile, which are obtained by fluorinating tetrachloroterephthalonitrile and tetrachloroisophthalonitrile obtained by chlorinating terephthalonitrile and isophthalonitrile. When tetrafluoroterephthalonitrile is reacted under the same conditions as in case of p-aminomethylbenzonitrile synthesis, 4-aminomethyl-2,3,5,6-tetrafluorobenzonitrile can be obtained at high-performance liquid chromatography area percentage of 38%.

Examples of the process of hydrating the aminomethyl group-containing benzonitrile compound represented by the general formula (I):

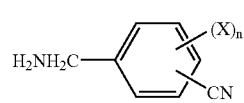

(I)

wherein —CN and —X represent a substituent on the benzene ring and —CN exits at the meta- or para-position of —CH$_2$NH$_2$, X represents a chlorine atom or a fluorine atom, and n represents an integer of 0 to 4, provided that, when n is 2 or more, X may be the same or different, used in the present invention includes:

(1) a process of hydrating a nitrile group in the presence of sulfuric acid;

(2) a process of hydrating a nitrile group in an organic solvent in the presence of a basic compound;

(3) a process of hydrating a nitrile group in the presence of hydrogen peroxide; and (4) a process of hydrating a nitrile group in the presence of a sponge Cu.

The above processes (1) to (4) will now be described.

(1) Process of Hydrating a Nitrile Group in the Presence of Sulfuric Acid

Sulfuric acid used in this process is preferably concentrated sulfuric acid, but may contain water described below, which is allowed to coexist. The amount of sulfuric acid is an amount enough to dissolve the benzonitrile compound as the raw material. When the amount is too small, a reaction product is deposited and it becomes difficult to handle. On the other hand, when using it in an excess amount, it is not preferred in view of the environment because the amount of wastes increases. Although optimum amount varies depending on the solubility of the aminomethyl group-containing benzonitrile as the raw material, the amount is preferably from 1 to 20 times, and more preferably from 2 to 10 times, by weight larger than that of the aminomethyl group-containing benzonitrile compound as the raw material.

When the reaction temperature is low, the reaction proceeds slowly. On the other hand, when the reaction temperature is high, the aminomethyl group-containing benzamide compound as the product is hydrolyzed and the yield is lowered. Therefore, the reaction temperature is preferably from 0 to 80° C., and more preferably from 5 to 60° C.

During the reaction, water is allowed to coexist in an amount required for hydration reaction. The amount of water, which is allowed to coexist, is preferably from 1 to 50 mol, and more preferably from 1.1 to 20 mol, per mol of the aminomethyl group-containing benzonitrile compound as the raw material. An amino group-containing benzonitrile compound which may contain water can also be used.

Since the aminomethyl group-containing benzamide compound thus produced exists in the form of an acidic salt, it is isolated and purified by neutralizing the acidic salt, concentrating water and collecting the deposited crystal with filtration. In case an inorganic salt is contained in the crystal collected by filtration, it can be isolated and purified by repeating an operation of recrystallization from water and drying the crystal collected by filtration.

(2) Process of Hydrating a Nitrile Group in a Solvent in the Presence of a Basic Compound In case of the process (2), the basic compound to be used is preferably a hydroxide of an alkali metal or an alkali earth metal, such as sodium hydroxide, potassium hydroxide or calcium hydroxide. The amount is preferably to from 0.01 to 5 times, and more preferably 0.02 to 2 times, by weight larger than that of the aminomethyl group-containing benzonitrile to be used.

As the organic solvent, any solvent can be used as far as it does not exert an adverse influence on the reaction and an alcohol-type solvent is suitable in view of the solubility of the raw material and the basic compound. Specific examples of the alcohol solvent include alkyl alcohol such as methanol, ethanol, isopropanol, or tert-butanol; alicyclic alcohol such as cyclohexyl alcohol; and aromatic alcohol such as benzyl alcohol.

During the reaction, water is allowed to coexist in an amount required for hydration reaction. The amount of water, which is allowed to coexist, is preferably from 1 to 20 mol, and more preferably from 1.1 to 10 mol, per mol of the aminomethyl group-containing benzonitrile compound as the raw material. An amino group-containing benzonitrile compound which may contain water can also be used.

The reaction temperature varies depending on the kind of the solvent to be used, but is preferably from 20° C. to the boiling point of the solvent, and more preferably from 40° C. to the boiling point of the solvent.

The aminomethyl group-containing benzamide compound thus produced can be isolated and purified by neutralizing a basic compound used, distilling off the solvent at low temperature under reduced pressure, recrystallizing from water and drying the crystal collected by filtration.

(3) Process of Hydrating a Nitrile Group in the Presence of a Hydrogen Peroxide

This reaction is a reaction which is reported by Radziszewski [Rer., 18, 355 (1885)] and known for long, however, it is unexpected to employ hydrogen peroxide as an oxidizing agent in a compound having an amino group, such as the compound of the present invention.

Although hydrogen peroxide is used in an amount of 2 mol per mol of a benzonitrile compound as a raw material, theoretically, the amount needed varies depending on the reaction conditions. The amount of hydrogen peroxide used in the present invention is preferably from 1.5 to 3.5 mol, and more preferably from 1.6 to 2.5 mol, per mol of the raw material so that the reaction is completed and the residual amount of hydrogen peroxide is reduced.

When the reaction temperature is low, the reaction proceeds slowly. On the other hand, when the reaction temperature is high, the aminomethyl group-containing benzamide compound as the product is likely to be hydrolyzed and also the reaction between an aminomethyl group and hydrogen peroxide is accelerated and the yield is lowered. Therefore, the reaction temperature is preferably from 0 to 60° C., and more preferably from 1 to 40° C.

In case of the process (3), a basic compound is preferably used as a catalyst. The basic compound is preferably a hydroxide of an alkali metal or an alkali earth metal, such as sodium hydroxide, potassium hydroxide or calcium hydroxide. The amount may be any amount as far as sufficient reaction rate can be obtained, but is preferably to from 0.01 to 1.5 times, and more preferably 0.05 to 1.0 times, by mol larger than that of the aminomethyl group-containing benzonitrile to be used.

As the reaction solvent, water is used and may be supplied in the form of hydrogen peroxide water. Also the reaction solvent may contain the other solvent as far as it does not exert an adverse influence on the reaction as well as isolation and purification. A water containing aminomethyl group-containing benzonitrile compound can also be used.

The amount of water is preferably from 1 to 20 times, and more preferably from 2 to 10 times, by weight larger than that of the aminomethyl group-containing benzonitrile compound to be used.

With respect to isolation and purification of the aminomethyl group-containing benzamide compound thus produced, the crystal is deposited or dissolved according to the concentration. In case the crystal is deposited, the crystal is collected by filtration and, if necessary, an operation of recrystallization from water is conducted. In case the crystal is dissolved, the compound can be isolated and purified by concentrating water, collecting the deposited crystal by filtration, optionally repeating an operation of recrystallization from water and drying the crystal collected by filtration.

(4) Process of Hydrating a Nitrile Group in the Presence of a Sponge Cu

The amount of a sponge copper catalyst used herein may be any amount as far as sufficient reaction rate can be obtained, but is preferably from 0.01 to 5 times, and more preferably 0.05 to 3 times, by weight larger than that of the aminomethyl group-containing benzonitrile compound as the raw material. The solvent to be used is preferably water, or a combination of an alcohol-type solvent and water required for hydration reaction. In this case, the reaction proceeds without adding an acid or a basic compound.

The amount of the solvent to be used is preferably from 2 to 100 times, and more preferably 3 to 20 times, by weight larger than that of the aminomethyl group-containing benzonitrile compound as the raw material. The reaction temperature is preferably from 5 to 160° C., and more preferably from 30 to 120° C. With respect to the reaction pressure, the reaction can be conducted at normal pressure or under pressure.

With respect to isolation and purification of the aaminomethyl group-containing benzamide compound thus produced, the crystal is deposited or dissolved according to the concentration. In case the crystal is deposited, the crystal is collected by filtration and, if necessary, an operation of recrystallization from water is conducted. In case the crystal is dissolved, the compound can be isolated and purified by concentrating water, collecting the deposited crystal by filtration, optionally repeating an operation of recrystallization from water and drying the crystal collected by filtration.

The operation of recrystallization or crystallization from water in the respective processes (1) to (4) is conducted by the following reasons. That is, it is effective to remove impurities such as aminomethyl group-containing benzoic acid produced as a result of hydrolysis of an amide group of the aminomethyl group-containing benzamide compound during the isolation operation.

In the present invention, raw materials such as aminomethyl group-containing benzonitrile, solvent, catalyst and reaction base (for example, alkali or hydrogen peroxide) may be added and mixed in any manner.

EXAMPLES

The following Examples illustrate the present invention in detail, but are not intended to limit the present invention.

In the analysis of products, high-performance liquid chromatography was used. The conditions are shown below.

<Conditions of High-Performance Liquid Chromatography>
Column: Shodex® (manufactured by SHOWA DENKO K.K.) C18M-4E+precolumn
Column temperature: column oven: 40° C.
Eluent: water/acetonitrile/acetic acid=2500/500/15 (ml)+sodium 1-octanesulfonate: 6.45 g
Eluent flow rate: 1 ml/min
Detector: UV (230 nm)

Example 1

In a reactor equipped with a motor-driven stirrer, 3450 g of concentrated sulfuric acid (reagent, purity: 98%) was charged and 1148 g of a water containing p-aminomethylbenzonitrile (958.6 g/7.253 mol as p-aminomethylbenzonitrile, purity: 83.5%, moisture: 189.4 g/10.522 mol) was gradually added so that the reaction temperature reaches 40 to 50° C., followed by mixing with stirring at 50° C. for 3 hours. After the completion of the reaction, 1440 g of water was added and the solution was stirred at 40° C. for one hour, then at room temperature overnight. The deposited crystal was collected by filtration and suspended in 4000 g of water and then neutralized by slowly adding 2117 g of potassium hydroxide (reagent, purity: 85%) while maintaining the temperature at 40 to 50° C.

The deposited p-aminomethylbenzamide-containing potassium sulfate crystal was collected by filtration and then cooled to 5° C. The deposited crystal was collected by filtration and then dried to obtain 521.6 g of p-aminomethylbenzamide.

An operation of recrystallization from the filtered p-aminomethylbenzamide-containing potassium sulfate crystal was repeated five times to obtain 421.7 g of p-aminomethylbenzamide (total yield based on p-aminomethylbenzonitrile was 84%).

The purity of p-aminomethylbenzamide determined by analyzing using high-performance liquid chromatograph was 97% or higher.

Example 2

In a reactor equipped with a motor-driven stirrer, 416 g of tert-butanol, 31.9 of potassium hydroxide (reagent, purity: 85%) and 59.5 g of a water containing p aminomethylbenzonitrile (50.0 g/0.378 mol as p-aminomethylbenzonitrile, purity: 84%, moisture: 9.5 g/0.528 mol) were charged in sequence and stirred at 800C for 2 hours. After the completion of the reaction, the reaction solution was cooled to room temperature and neutralized with 193.7 g of an aqueous 15 wt % sulfuric acid solution, and then the resulting potassium sulfate crystal was removed by filtration in a hot state at 70° C. Tert-butanol in the resulting filtrate was concentrated under reduced pressure, cooled to 5° C. and then stirred for 2 hours. The deposited crystal was collected by filtration and then dried to obtain 46.6 g of p-aminomethylbenzamide (yield based on p-aminomethylbenzonitrile was 82%).

The purity of p-aminomethylbenzamide determined by analyzing using high-performance liquid chromatograph was 99% or higher.

Example 3

In a reactor equipped with a motor-driven stirrer, 45 g of water, 1.38 g of sodium hydroxide (reagent, purity: 96%) and 43.56 g of p-aminomethylbenzonitrile were charged in this sequence and then stirred at room temperature. 74.8 g of 30 wt % hydrogen peroxide water was gradually added so that the reaction temperature reaches 30° C. or lower, followed by mixing with stirring. After foaming and temperature rise were terminated, the reaction solution was cooled to 5° C. The deposited crystal was collected by filtration and then dried to obtain 41.92 g of p-aminomethylbenzamide (yield based on p-aminomethylbenzonitrile: 81%). The purity of p-aminomethylbenzamide determined by analyzing using high-performance liquid chromatograph was 97%.

Example 4

In a 100 ml autoclave (manufactured by Nitto Koatsu Co., Ltd., material: SUS-316), 43 g of water, 11.5 g of a water-containing p-aminomethylbenzonitrile (10 g as p-aminomethylbenzonitrile, purity: 86.7%.) and 2.0 g of sponge copper (R-300C, manufactured by NIKKO RICA CORPORATION) were charged and, after sealing the autoclave, the atmosphere in the autoclave was replaced by nitrogen and the reaction was conducted at 100° C. for 6 hours. After the completion of the reaction, the catalyst was collected by filtration and the filtrate was cooled to 5° C., and then the crystal was collected by filtration. 10.0 g of the resulting crystal (wet form, containing 8.05 g of p-aminomethylbenzamide) was suspended in 43 g of water and dissolved with heating to 70° C., followed by cooled again to 5° C., filtration and further drying to obtain 7.99 g of p-aminomethylbenzamide (yield based on p-aminomethylbenzonitrile: 71%). The purity of p-aminomethylbenzamide determined by analyzing using high-performance liquid chromatograph was 99% or higher.

Example 5

The same operation as in Example 3 was conducted, except that m-aminomethylbenzonitrile was used in place of p-aminomethylbenzonitrile. As a result, 38.11 g of m-aminomethylbenzamide was obtained (yield based on m-aminomethylbenzonitrile: 77%). The purity of m-aminomethylbenzamide determined by analyzing using high-performance liquid chromatograph was 97%.

INDUSTRIAL APPLICABILITY

According to the present invention, an aminomethyl group-containing benzamide compound with high purity can be produced with high yield by the hydration reaction of an aminomethyl group-containing benzonitrile compound which is easily obtained from a phthalonitrile compound.

The invention claimed is:

1. A process for producing an aminomethyl group-containing benzamide compound represented by the general formula (II):

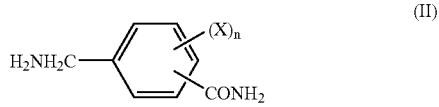

wherein —CONH$_2$ and —X represent a substituent on the benzene ring and —CONH$_2$ exists at the meta- or para-position of —CH$_2$NH$_2$, and X and n are as defined below, which comprises hydrating an aminomethyl group-containing benzonitrile compound represented by the general formula (I):

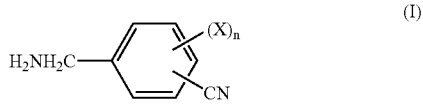

wherein —CN and —X represent a substituent on the benzene ring and —CN exists at the meta- or para-position of —CH$_2$NH$_2$, X represents a chlorine atom or a fluorine atom, and n represents an integer of 0 to 4, provided that, when n Is 2 or more, X may be the same or different,
wherein the hydration is conducted in the presence of hydrogen peroxide.

2. The process according to claim 1, wherein the aminomethyl group-containing benzonitrile compound of the general formula (I) is m- or p-aminomethylbenzonitrile and the aminomethyl group-containing benzamide compound of the general formula (II) is m- or p-aminomethylbenzamide.

3. The process according to claim 1, which uses an aminomethyl group-containing benzonitrile compound represented by the general formula (I):

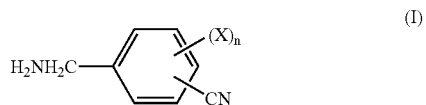

wherein —CN and —x represent a substituent on the benzene ring and —CN exists at the meta- or para-position of —CH$_2$NH$_2$, and X and n are as defined below, which is obtained by selectively reducing either of nitrile groups of a phthalonitrile compound represented by the general formula (III):

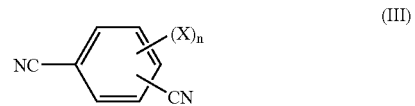

wherein —CN and —X represent a substituent on the benzene ring, two —CN(s) exist at the meta- or para-position, X represents a chlorine atom or a fluorine atom, and n represents an integer of 0 to 4, provided that, when n is 2 or more, X may be the same or different.

* * * * *